US010041076B2

(12) United States Patent
Kandimalla et al.

(10) Patent No.: US 10,041,076 B2
(45) Date of Patent: *Aug. 7, 2018

(54) IMMUNE REGULATORY OLIGONUCLEOTIDE (IRO) COMPOUNDS TO MODULATE TOLL-LIKE RECEPTOR BASED IMMUNE RESPONSE

(71) Applicant: Idera Pharmaceuticals, Inc., Cambridge, MA (US)

(72) Inventors: Ekambar R. Kandimalla, Hopkinton, MA (US); Daqing Wang, Bedford, MA (US); Dong Yu, Westboro, MA (US); Ireneusz Nowak, Allston, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/209,333

(22) Filed: Jul. 13, 2016

(65) Prior Publication Data

US 2016/0312225 A1   Oct. 27, 2016

Related U.S. Application Data

(60) Continuation of application No. 14/990,929, filed on Jan. 8, 2016, which is a division of application No. 14/149,899, filed on Jan. 8, 2014, now Pat. No. 9,260,719.

(60) Provisional application No. 61/750,014, filed on Jan. 8, 2013.

(51) Int. Cl.
| *A61K 39/39* | (2006.01) |
| *A61K 45/06* | (2006.01) |
| *C12N 15/117* | (2010.01) |
| *A61K 9/00* | (2006.01) |
| *A61K 31/711* | (2006.01) |
| *A61K 31/7115* | (2006.01) |
| *A61K 39/00* | (2006.01) |

(52) U.S. Cl.
CPC .......... *C12N 15/117* (2013.01); *A61K 9/0019* (2013.01); *A61K 31/711* (2013.01); *A61K 31/7115* (2013.01); *A61K 39/39* (2013.01); *A61K 45/06* (2013.01); *A61K 2039/55561* (2013.01); *C12N 2310/17* (2013.01); *C12N 2310/335* (2013.01); *C12N 2310/336* (2013.01); *C12N 2310/3341* (2013.01); *C12N 2320/30* (2013.01); *C12N 2320/31* (2013.01); *C12N 2710/24043* (2013.01)

(58) Field of Classification Search
None
See application file for complete search history.

(56) References Cited

U.S. PATENT DOCUMENTS

| 7,105,495 | B2* | 9/2006 | Agrawal | C07H 21/00 424/1.11 |
|---|---|---|---|---|
| 7,176,296 | B2* | 2/2007 | Agrawal | A61K 39/39 424/278.1 |
| 7,276,489 | B2* | 10/2007 | Agrawal | A61K 39/39 514/44 R |
| 7,354,907 | B2* | 4/2008 | Agrawal | C07H 21/02 514/44 A |
| 7,405,285 | B2* | 7/2008 | Agrawal | A61K 31/711 536/22.1 |
| 7,407,944 | B2* | 8/2008 | Agrawal | A61K 39/39 424/184.1 |
| 7,427,405 | B2* | 9/2008 | Agrawal | A61K 39/39 424/277.1 |
| 7,470,674 | B2* | 12/2008 | Agrawal | A61K 39/39 424/184.1 |
| 7,498,425 | B2* | 3/2009 | Agrawal | A61K 39/39 424/130.1 |
| 7,498,426 | B2* | 3/2009 | Agrawal | A61K 39/39 424/9.81 |
| 7,517,862 | B2* | 4/2009 | Agrawal | A61K 39/39 424/130.1 |
| 7,566,702 | B2* | 7/2009 | Agrawal | A61K 39/39 514/44 R |
| 7,595,305 | B2* | 9/2009 | Agrawal | C07H 21/00 514/44 R |
| 7,632,822 | B2* | 12/2009 | Agrawal | C07H 21/00 514/44 R |

(Continued)

FOREIGN PATENT DOCUMENTS

WO    WO 03/035836 A2 *  5/2003
WO    WO 2009/154609 A1 * 12/2009
(Continued)

OTHER PUBLICATIONS

Hanauer, Inflamm. Bowel Dis., Jan. 2006, 12/Suppl. 1:S3-S9.*
Kandimalla et al, Nucleic Acid Research, 2013, 41/6:3947-3961.*
Abreu MT, Arnold ET, Thomas LS, et al., "TLR4 and MD-2 expression is regulated by immune-mediated signals in human intestinal epithelial cells." J Biol Chem. Jun. 7, 2002;277(23):20431-7.
Alzabin S, Kong P, Medghalchi M, et al., "Investigation of the role of endosomal Toll-like receptors in murine collagen-induced arthritis reveals a potential role for TLR7 in disease maintenance." Arthritis Res Ther. 2012;14:R142.
Barnich N, Darfeuille-Michaud A., "Role of bacteria in the etiopathogenesis of inflammatory bowel disease." World J Gastroenterol. Nov. 14, 2007;13(42):5571-6.

(Continued)

Primary Examiner — Nita M. Minnifield
(74) Attorney, Agent, or Firm — Jones Day

(57) ABSTRACT

The invention provides immune regulatory oligonucleotides (IRO) as antagonist of TLRs and methods of use thereof. These IROs have unique sequences that inhibit TLR-mediated signaling in response to a TLR ligand or TLR agonist. The methods may have use in the prevention and treatment of cancer, an autoimmune disorder, airway inflammation, inflammatory disorders, infectious disease, skin disorders, allergy, asthma or a disease caused by a pathogen.

20 Claims, 3 Drawing Sheets

(56) References Cited

U.S. PATENT DOCUMENTS

| | | | | |
|---|---|---|---|---|
| 7,709,617 | B2* | 5/2010 | Kandimalla | A61K 38/2013 536/22.1 |
| 7,749,975 | B2* | 7/2010 | Agrawal | A61K 39/39 424/130.1 |
| 7,776,834 | B2* | 8/2010 | Agrawal | A61K 31/70 424/184.1 |
| 7,786,089 | B2* | 8/2010 | Kandimalla | A61K 48/00 435/325 |
| 7,790,168 | B2* | 9/2010 | Kandimalla | A61K 31/7088 424/184.1 |
| 7,812,000 | B2* | 10/2010 | Agrawal | A61K 39/39 424/184.1 |
| 7,824,696 | B2* | 11/2010 | Kandimalla | A61K 31/7088 424/278.1 |
| 7,833,538 | B2* | 11/2010 | Kandimalla | A61K 31/7088 424/278.1 |
| 7,851,453 | B2* | 12/2010 | Agrawal | C07H 21/00 514/44 R |
| 7,851,454 | B2* | 12/2010 | Agrawal | C07H 21/02 424/130.1 |
| 7,863,250 | B2* | 1/2011 | Agrawal | C07H 21/00 514/44 R |
| 7,884,197 | B2* | 2/2011 | Kandimalla | C12N 15/117 424/9.2 |
| 7,932,367 | B2* | 4/2011 | Kandimalla | A61K 31/7088 424/184.1 |
| 7,960,362 | B2* | 6/2011 | Kandimalla | A61K 31/711 424/184.1 |
| 8,008,267 | B2* | 8/2011 | Kandimalla | C12N 15/117 514/44 R |
| 8,030,462 | B2* | 10/2011 | Kandimalla | A61K 31/7088 424/184.1 |
| 8,153,608 | B2* | 4/2012 | Agrawal | C07H 21/00 514/44 A |
| 8,188,261 | B2* | 5/2012 | Kandimalla | A61K 31/7105 536/24.1 |
| 8,202,850 | B2* | 6/2012 | Agrawal | A61K 39/39 424/184.1 |
| 8,357,665 | B2* | 1/2013 | Kandimalla | A61K 48/00 514/44 R |
| 8,377,898 | B2* | 2/2013 | Kandimalla | A61K 31/7052 514/44 R |
| 8,383,598 | B2* | 2/2013 | Kandimalla | A61K 31/7052 514/44 R |
| 8,399,423 | B2* | 3/2013 | Kandimalla | A61K 31/711 514/44 R |
| 8,426,375 | B2* | 4/2013 | Kandimalla | A61K 31/7088 514/44 R |
| 8,476,416 | B2* | 7/2013 | Kandimalla | A61K 31/7088 424/184.1 |
| 8,486,908 | B2* | 7/2013 | Kandimalla | A61K 31/7115 424/184.1 |
| 8,713,253 | B1* | 4/2014 | Botchek | G11B 33/126 711/114 |
| 8,853,177 | B2 | 10/2014 | Zhu et al. | |
| 8,940,310 | B2 | 1/2015 | Barrat et al. | |
| 8,987,221 | B2* | 3/2015 | Zhu | A61K 31/7088 514/44 R |
| 9,096,858 | B2* | 8/2015 | Kandimalla | A61K 31/7115 |
| 9,206,430 | B2* | 12/2015 | Kandimalla | A61K 48/00 |
| 9,243,050 | B2* | 1/2016 | Kandimalla | C12N 15/117 |
| 9,260,719 | B2* | 2/2016 | Kandimalla | A61K 31/7115 |
| 9,415,046 | B2 | 8/2016 | Mehal et al. | |
| 9,453,228 | B2* | 9/2016 | Kandimalla | A61K 48/00 |
| 2009/0060898 | A1* | 3/2009 | Kandimalla | A61K 48/00 424/130.1 |
| 2010/0098685 | A1 | 4/2010 | Zhu et al. | |
| 2011/0171209 | A1* | 7/2011 | Zhu | A61K 31/7088 424/133.1 |
| 2012/0128699 | A1* | 5/2012 | Kandimalla | A61K 31/7115 424/173.1 |
| 2012/0225931 | A1 | 9/2012 | Mehal et al. | |
| 2013/0156814 | A1 | 6/2013 | Barrat et al. | |
| 2013/0267583 | A1* | 10/2013 | Kandimalla | A61K 48/00 514/44 R |
| 2014/0004100 | A1* | 1/2014 | Kandimalla | A61K 31/7115 424/130.1 |
| 2014/0193396 | A1* | 7/2014 | Kandimalla | A61K 31/7115 424/130.1 |
| 2014/0308300 | A1* | 10/2014 | Kandimalla | C12N 15/117 424/174.1 |
| 2016/0138022 | A1* | 5/2016 | Kandimalla | A61K 48/00 424/130.1 |
| 2016/0215287 | A1* | 7/2016 | Kandimalla | A61K 31/7115 |
| 2016/0312225 | A1* | 10/2016 | Kandimalla | A61K 9/0019 |
| 2017/0233741 | A1* | 8/2017 | Kandimalla | A61K 31/7115 424/130.1 |
| 2017/0268006 | A1* | 9/2017 | Agrawal | C12N 15/117 |
| 2017/0369885 | A1* | 12/2017 | Glasmacher | C12Q 1/6816 |
| 2018/0023085 | A1* | 1/2018 | Kandimalla | A61K 45/06 |

FOREIGN PATENT DOCUMENTS

| | | |
|---|---|---|
| WO | WO 2011/041311 | 4/2011 |
| WO | WO 2011/159958 | 12/2011 |
| WO | WO 2012/068470 | 5/2012 |

OTHER PUBLICATIONS

Bas, D. et al., "Collagen Antibody-Induced Arthritis Evokes Persistent Pain with Spinal Glial Involvement and Transient Prostaglandin Dependency." 2012, Arthritis & Rheumatism, 64(12):3886-3896.

Berkowitz D. et al., Increased Toll-like receptor 9 expression by B cells from inflammatory bowel disease patients. Hum Immunol. 2013;74:1519-1523.

Boirivant M, Pallone F, Di Giacinto C, et al, "Inhibition of Smad7 with a specific antisense oligonucleotide facilitates TGF-beta1-mediated suppression of colitis." Gastroenterology. Dec. 2006;131(6):1786-98.

Cario, "Toll-like receptors in inflammatory bowel diseases: A decade later," Inflamm. Bowel. Dis., 2010, vol. 16, No. 9, 1583-1597.

Cattaruzza, F et al., "Cathepsin S Is Activated During Colitis and Causes Visceral Hyperalgesia by a $PAR_2$-Dependent Mechanism in Mice." 2011, Gastroenterology, 141:1864-1874.

Chan, J. R. et al., "IL-23 stimulates epidermal hyperplasia via TNF and IL-20R2-dependent mechanisms with implications for psoriasis pathogenesis." 2006, The Journal of Experimental Medicine, 203(12):2577-2587.

Cook, D.N. et al, "Toll-like receptors in the pathogenesis of human disease." 2004, Nature Immunol. 5:975-979.

Cros J, Cagnard N, Woollard K, et al., "Human CD14dim Monocytes Patrol and Sense Nucleic Acids and Viruses via TLR7 and TLR8 Receptors." Immunity. 2010;33:1-12.

Dai, R. et al., "Identification of a Common Lupus Disease-Associated microRNA Expression Pattern in Three Different Murine Models of Lupus." 2010 PLoS ONE, 5(12):1-8.

Demaria O, Pagni P, Traub S, et al. "TLR8 deficiency leads to autoimmunity in mice." J Clin Invest. 2010;120:3651-3662.

Galligan, C. et al., "Circulating Fibrocytes Contribute to the Pathogenesis of Collagen Antibody-Induced Arthritis," 2012, Arthritis and Rheumatism, 64(11):3583-3593.

Green N, Marshak-Rothstein A., "Toll-like receptor driven B cell activation in the induction of systemic autoimmunity." A Sem Immunol. 2011;23:106-112.

Guiducci, C., et al., "TLR recognition of self nucleic acid hampers glucocorticoid activity in lupus." Nature, 2010, 465:937-942.

Hari A, Flach T, Shi Y, et al. "Toll-Like Receptors: Role in Dermatological Disease." Mediat Inflamm. 2010;437246.

Hou, L. et al., "Oral Administration of Artemisinin Analogy SM934 Ameriorates Lupus Syndromes in MRL/lpr Mice by Inhibiting Th1 and Th17 Cell Responses." 2011, Arthritis and Rheumatism, 63(8):2445-2455.

Kandimalla et al., "Design, synthesis and biological evaluation of novel antagonist compounds of Toll-like receptors 7, 8, and 9," Nucleic Acids Research, 2013, vol. 41, No. 6, 3947-3961.

(56) References Cited

OTHER PUBLICATIONS

Kim, J.et al., "The Immunopathogenesis of Psoriasis." Dermatol. Clin. 2005; 33:13-23.
Koboziev, I. et al., "Pharmacological Intervention Studies Using Mouse Models of the Inflammatory Bowel Diseases: Translating Preclinical Data into New Drug Therapies." 2011, Inflamm. Bowel. Dis. 17(5):1229-1245.
Kono D, Haraldsson M, Lawson B, et al., "Endosomal TLR signaling is required for anti-nucleic acid and rheumatoid factor autoantibodies in lupus." Proc Natl Acad Sci USA. 2009;106:12061-12066.
Leadbetter, E., et al., "Chromatin-IgG complexes activate B cells by dual engagement of IgM and Toll-like receptors." Nature, 2002, 416:603-607.
Lin, Y. et al., "Glutamate Transporter GLT-1 Upregulation Attenuates Visceral Nociception and Hyperalgesia via Spinal Mechanisms Not Related to Anti-Inflammatory or Probiotic Effects." 2011, Pain Research and Treatment, Article ID 507029 pp. 1-10.
Manzel L, Strekowski L, Ismail F, et al., "Antagonism of Immunostimulatory CpG-Oligodeoxynucleotides by 4-Aminoquinolines and Other Weak Bases: Mechanistic Studies." J Pharmacol Exp Ther. 1999;291:1337-1347.
Marshak-Rothstein A, Rifkin I., "Immunologically Active Autoantigens: The Role of Toll-Like Receptors in the Development of Chronic Inflammatory Disease." Annu Rev Immunol. 2007;25:419-441.
Means, T., et al., "Human lupus autoantibody-DNA complexes activate DCs through cooperation of CD32 and TLR9," J.Clin. Invest., 1-11.
Mizoguchi, A., "Animal Models of Inflammatory Bowel Disease." 2012, Progress in Molecular Biology and Translational Science, 105: 263-320.
Monteleone G, Fantini MC, Onali S, et al. Phase I clinical trial of Smad7 knockdown using antisense oligonucleotide in patients with active Crohn's disease. Mol Ther. Apr. 2012;20(4):870-876.
Monteleone G, Caruso R, Pallone F. Targets for new immunomodulation strategies in inflammatory bowel disease. Autoimmun Rev. Jan. 2014;13(1):11-4.
Obermeier F, Hofmann C, Falk W., "Inflammatory bowel diseases: when natural friends turn into enemies—the importance of CpG motifs of bacterial DNA in intestinal homeostasis and chronic intestinal inflammation." Int J Inflamm. 2010;2010:641910.
Oestergaard, S. et al., "Evaluation of Cartilage and Bone Degradation in a Murine collagen Antibody-induced Arthritis Model," 2008, Scandinavian Journal of Immunology, 67:304-312.
Prinz M, Garbe F, Schmidt H, et al., "Innate immunity mediated by TLR9 modulates pathogenicity in an animal model of multiple sclerosis." J Clin Invest. 2006;116:456-464.
Rönnblom L, Alm G, Eloranta M., "The type I interferon system in the development of lupus." Semin Immunol. 2011;23:113-121.
Sacre K, Criswell L, McCune J., "Hydroxychloroquine is associated with impaired interferon-alpha and tumor necrosis factor-alpha production by plasmacytoid dendritic cells in systemic lupus erythematosus." Arthr Res Ther. 2012;14:R155.
Savarese, E., et al., "U1 small nuclear ribonucleoprotein immune complexes induce type I interferon in plamacytoid dendritic cells through TLR7." Blood, 107(8): 3229-3234.
Steenholdt C, Andresen L, Pedersen G, et al., "Expression and function of toll-like receptor 8 and Tollip in colonic epithelial cells from patients with inflammatory bowel disease." Scand J Gastroenterol, 2009;44(2):195-204.
Stump, K. et al., "A highly selective, orally active inhibitor of Janus kinase 2, CEP-33779, ablates disease in two mouse models of rheumatoid arthritis." 2011, Arthritis Research & Therapy, 13:R68, pp. 1-15.
Sun S, Rao N, Venable J, et al., "TLR7/9 Antagonists as Therapeutics for Immune-Mediated Inflammatory Disorders." Inflamm Allergy Drug Targets. 2007;6:223-235.
Te Velde, A. A. et al., "Critical Appraisal of the Current Practice in Murine TNBS-induced Colitis." 2006, Inflamm. Bowel. Dis., 12:995-999.
Vamadevan AS, Fukata M, Arnold ET, et al., Regulation of Toll-like receptor 4-associated MD-2 in intestinal epithelial cells: a comprehensive analysis. Innate Immun. Apr. 2010;16(2):93-103.
Vollmer, J., et al., "Immune stimulation mediated by autoantigen binding sites within small nuclear RNAs involves Toll-like receptors 7 and 8." J. Exp. Med., 2005, 202(11):1575-1585.
Willis R, Seif A, McGwin G, et al., "Effect of hydroxychloroquine treatment on pro-inflammatory cytokines and disease activity in SLE patients: data from LUMINA (LXXV), a multiethnic US cohort." Lupus. 2012;21:830-835.
Wu H, Sawaya H, Binstadt B, et al., "Inflammatory arthritis can be reined in by CpG-induced DC-NK cell cross talk." J Exp Med. 2007;204:1911-1922.
Zheng B, Morgan ME, van de Kant HJ, et al. Transcriptional modulation of pattern recognition receptors in acute colitis in mice. Biochim Biophys Acta. Dec. 2013;1832(12):2162-72.

\* cited by examiner

| Antagonist # | IC$_{50}$, μg/ml | | | |
|---|---|---|---|---|
| | TLR7 | TLR8 | TLR9 | TLR4 |
| 2 | 0.005 | 0.016 | 0.246 | 4.674 |
| 6 | 0.005 | 0.010 | 0.173 | 13.68 |
| 7 | 0.005 | 0.010 | 0.253 | 2.55 |
| 12 | 0.005 | 0.005 | 0.229 | 5.116 |
| 13 | 0.086 | 0.025 | 0.131 | 7.323 |
| 16 | 0.010 | 0.021 | 0.368 | 1.407 |

FIG. 3

IMMUNE REGULATORY OLIGONUCLEOTIDE (IRO) COMPOUNDS TO MODULATE TOLL-LIKE RECEPTOR BASED IMMUNE RESPONSE

RELATED APPLICATIONS

This application is a continuation of U.S. application Ser. No. 14/990,929, filed on Jan. 8, 2016, which is a divisional of U.S. application Ser. No. 14/149,899, filed on Jan. 8, 2014 (now U.S. Pat. No. 9,260,719), which claims the benefit of U.S. Provisional Patent Application No. 61/750,014, filed on Jan. 8, 2013, the contents of which are incorporated herein by reference in their entirety.

BACKGROUND OF THE INVENTION

Field of the Invention

The invention generally relates to the field of immunology and immunotherapy, and more specifically to immune regulatory oligonucleotide (IRO) compositions and their use for inhibition and/or suppression of Toll-like Receptor-mediated immune responses. In particular, the invention relates to antagonists of Toll-Like Receptor 9 (TLR9), TLR7, and/or TLR8 that uniquely inhibit cytokines normally produced through TLR9, TLR7, and/or TLR8 stimulation.

SUMMARY OF THE RELATED ART

Toll-like receptors (TLRs) are present on many cells of the immune system and have been shown to be involved in the innate immune response (Hornung, V. et al., (2002) J. Immunol. 168:4531-4537). In vertebrates, or mammals, this family consists often proteins called TLR1 to TLR10, which are known to recognize pathogen associated molecular patterns from bacteria, fungi, parasites, and viruses (Poltorak, a et al. (1998) Science 282.2085-2088; Underhill, D. M., et al. (1999) Nature 401:811-815; Hayashi, F. et. al (2001) Nature 410:1099-1103; Zhang, D. et al. (2004) Science 303.1522-1526; Meier, A et al. (2003) Cell. Microbiol. 5:561-570; Campos, M. A. et al. (2001) J. Immunol. 167: 416-423; Hoebe, K. et al. (2003) Nature 424: 743-748, Lund. J. (2003) J. Exp. Med 198:513-520; Heil, F. et al. (2004) Science 303.1526-1529; Diebold, S. S., et al. (2004) Science 303: 1529-1531; Hornung, V. et al (2004) J. Immunol. 173:5935-5943). TLRs are a key means by which mammals recognize and mount an immune response to foreign molecules and also provide a means by which the innate and adaptive immune responses are linked (Akira, S. et al. (2001) Nature Immunol. 2:675-680; Medzhitov, R. (2001) Nature Rev. Immunol. 1:135-145). TLRs have also been shown to play a role in the pathogenesis of many diseases, including autoimmunity, infectious disease, and inflammation (Cook, D. N. et al. (2004) Nature Immunol. 5:975-979) and the regulation of TLR-mediated activation using appropriate agents may provide a means for disease intervention.

Some TLRs are located on the cell surface to detect and initiate a response to extracellular pathogens and other TLRs are located inside the cell to detect and initiate a response to intracellular pathogens. Table 1 provides a representation of TLRs, their cellular location, and the known agonists therefore (Diebold, S. S. et al. (2004) Science 303:1529-1531; Liew, F. et al. (2005) Nature 5:446-458; Hemmi H et al. (2002) Nat Immunol 3:196-200; Jurk M et al., (2002) Nat Immunol 3:499; Lee J et al. (2003) Proc. Natl. Acad. Sci. USA 100:6646-6651); (Alexopoulou, L. (2001) Nature 413: 732-738).

TABLE 1

| TLR Molecule | Agonist |
|---|---|
| Cell Surface TLRs: | |
| TLR2 | bacterial lipopeptides |
| TLR4 | gram negative bacteria |
| TLR5 | motile bacteria |
| TLR6 | gram positive bacteria |
| Endosomal TLRs: | |
| TLR3 | double stranded RNA viruses |
| TLR7 | single stranded RNA viruses |
| TLR8 | single stranded RNA viruses |
| TLR9 | unmethylated DNA |

Certain unmethylated CpG motifs present in bacterial and synthetic DNA have been shown to activate the immune system and induce antitumor activity. (Tokunaga T et al., J. Natl. Cancer Inst. (1984) 72:955-962, Shimada S, et al., Jpn. H cancer Res, 1986, 77, 808-816; Yamamoto S, et al., Jpn. J. Cancer Res., 1986, 79, 866-73). Other studies using antisense oligonucleotides containing CpG dinucleotides have been shown to stimulate immune responses (Zhao Q, et al. (1996) Biochem. Pharmacol. 26:173-182). Subsequent studies demonstrated that TLR9 recognizes unmethylated CpG motifs present in bacterial and synthetic DNA (Hemmi, H. et al. (2000) Nature 408:740-745). Other modifications of CpG-containing phosphorothioate oligonucleotides can also affect their ability to act as modulators of immune response through TLR9 (see, e.g., Zhao et al., Biochem. Pharmacol. (1996) 51:173-182; Zhao et al. (1996) Biochem Pharmacol. 52:1537-1544; Zhao et al. (1997) Antisense Nucleic Acid Drug Dev. 7:495-502; Zhao et al (1999) Bioorg. Med. Chem. Lett. 9:3453-3458; Zhao et al. (2000) Bioorg. Med. Chem. Lett. 10:1051-1054; Yu, D. et al. (2000) Bioorg. Med. Chem. Lett. 10:2585-2588; Yu, D. et al. (2001) Bioorg. Med. Chem. Lett. 11:2263-2267; and Kandimalla, E. et al. (2001) Bioorg. Med. Chem. 9:807-813). In addition, structure activity relationship studies have allowed identification of synthetic motifs and novel DNA-based compounds that induce specific immune response profiles that are distinct from those resulting from unmethylated CpG dinucleotides. (Kandimalla, E. et al. (2005) Proc. Natl. Acad. Sci. USA 102:6925-6930. Kandimalla, E. et al. (2003) Proc. Nat. Acad. Sci. USA 100:14303-14308; Cong, Y. et al. (2003) Biochem Biophys Res. Commun. 310:1133-1139; Kandimalla, E. et al. (2003) Biochem. Biophys. Res. Commun. 306:948-953; Kandimalla, E. et al. (2003) Nucleic Acids Res. 31:2393-2400; Yu, D. et al. (2003) Bioorg. Med. Chem. 11:459-464; Bhagat, L. et al. (2003) Biochem. Biophys. Res. Commun. 300:853-861; Yu, D. et al. (2002) Nucleic Acids Res. 30:4460-4469; Yu, D. et al. (2002) J. Med. Chem. 45:4540-4548. Yu, D. et al. (2002) Biochem. Biophys. Res. Commun. 297:83-90; Kandimalla. E. et al. (2002) Bioconjug. Chem. 13:966-974; Yu, D. et al. (2002) Nucleic Acids Res. 30:1613-1619; Yu, D. et al. (2001) Bioorg. Med. Chem. 9:2803-2808; Yu, D. et al. (2001) Bioorg. Med. Chem. Lett. 11:2263-2267; Kandimalla, E. et al. (2001) Bioorg. Med. Chem. 9:807-813; Yu, D. et al. (2000) Bioorg. Med. Chem. Lett. 10:2585-2588; Putta, M. et al. (2006) Nucleic Acids Res. 34:3231-3238).

The selective localization of TLRs and the signaling generated therefrom, provides some insight into their role in the immune response. The immune response involves both an innate and an adaptive response based upon the subset of cells involved in the response. For example, the T helper (Th) cells involved in classical cell-mediated functions such as delayed-type hypersensitivity and activation of cytotoxic T lymphocytes (CTLs) are Th1 cells. This response is the body's innate response to antigen (e.g. viral infections, intracellular pathogens, and tumor cells), and results in a secretion of IFN-gamma and a concomitant activation of CTLs. Alternatively, the Th cells involved as helper cells for B-cell activation are Th2 cells. Th2 cells have been shown to be activated in response to bacteria and parasites and may mediate the body's adaptive immune response (e.g. IgE production and eosinophil activation) through the secretion of IL-4 and IL-5. The type of immune response is influenced by the cytokines produced in response to antigen exposure and the differences in the cytokines secreted by Th1 and Th2 cells may be the result of the different biological functions of these two subsets.

While activation of TLRs is involved in mounting an immune response, an uncontrolled stimulation of the immune system through TLRs may exacerbate certain diseases in immune compromised subjects. In recent years, several groups have shown the use of synthetic oligodeoxyoligonucleotides (ODNs) as inhibitors of inflammatory cytokines (Lenert, P. et al. (2003) DNA Cell Biol. 22(10): 621-631).

Using certain synthetic ODNs, Lenert et al. report the ability to produce inhibitory ODNs (Lenert, P. et al. (2003) DNA Cell Biol. 22(10):621-631). These inhibitory ODN require two triplet sequences, a proximal "CCT" triplet and a distal "GGG" triplet. In addition to these triplet-containing inhibitory ODNs, several groups have reported other specific DNA sequences that could inhibit TLR-9-mediated activation by CpG-containing ODNs. These "inhibitory" or "suppressive" motifs are rich in poly "G" (e.g. "GGGG") or "GC" sequences, tend to be methylated, and are present in the DNA of mammals and certain viruses (see e.g., Chen, Y., et al., Gene Ther. 8: 1024-1032 (2001); Stunz, L. L., Eur. J. Immunol. 32: 1212-1222 (2002). Duramad, O., et al., J. Immunol., 174: 5193-5200 (2005) and Jurk et. al (US 2005/0239733), describe a structure for inhibitory DNA oligonucleotides containing a GGGG motif within the sequences. Patole et al. demonstrate that GGGG containing ODNs will suppress systemic lupus (Patole, P. et al. (2005) J. Am. Soc. Nephrol. 16:3273-3280). Additionally, Gursel, I., et al., J. Immunol., 171: 1393-1400 (2003), describe repetitive TTAGGG elements, which are present at high frequency in mammalian telomeres, down-regulate CpG-induced immune activation. Shirota, H., et al., J. Immunol., 173: 5002-5007 (2004), demonstrate that synthetic oligonucleotides containing the TTAGGG element mimic this activity and could be effective in the prevention/treatment of certain Th1-dependent autoimmune diseases.

In contrast, some studies have called into question the view that poly G containing ODNs are acting as antagonists of TLRs. For example, U.S. Pat. No. 6,426,334, Agrawal et al., demonstrate that administering CpG oligonucleotides containing GGGG strings have potent antiviral and anticancer activity and that administration of these compounds will cause an increase in serum IL-12 concentration. Further, CpG oligos containing polyG sequences are known to induce immune responses through TLR9 activation (Verthelyi D et al, J Immunol. 166, 2372, 2001; Gursel M et al, J Leukoc Biol, 71, 813, 2001, Krug A et al, Eur J Immunol, 31, 2154, 2001) and show antitumor and antiviral activities (Ballas G K et al, J Immunol, 167, 4878, 2001; Verthelyi D et al, J Immunol, 170, 4717, 2003). In addition, polyG oligonucleotides are known to inhibit HIV and Rel A (Mc-Shan W M, et al, J Biol Chem., 267(8):5712-21, 1992; Rando, R F et al., J Biol Chem, 270(4):1754-60, 1995; Benimetskaya L, et al., Nucleic Acids Res., 25(13):2648-56, 1997); and ODNs containing an immune stimulatory CpG motif and 4 consecutive G nucleotides (known as class A ODNs) induce interferon-γ production and a Th1 shift in the immune response. Moreover, in preclinical disease models, Class A ODNs have been shown to induce a TLR-mediated immune response.

As an additional limitation, oligonucleotides containing guanosine strings have been shown to form tetraplex structures, act as aptamers, and inhibit thrombin activity (Bock L C et al., Nature, 355:564-6, 1992; Padmanabhan, K et al., J Biol Chem., 268(24):17651-4, 1993). Thus, it is not clear whether single-stranded or multiple-stranded structures are effective at suppressing TLR9 activation.

Kandimalla et al. (Ser. No. 11/549,048) describe a novel class of TLR antagonists that do not require a polyG sequence. Kandimalla et al. also describes the application of these novel compositions to treating and preventing various diseases and disorders (Ser. Nos. 11/549,048; 11/743,876; 12/140,334; 12/140,338; 12/244,199). However a challenge remains to develop additional TLR antagonists that do not require a polyG sequence and thus do not present the problem of forming secondary structures. Additionally, there are the challenges presented by the variability of diseases and the complexity of treating diseases and patients. This challenge may be solved through the design of new oligonucleotide-based compounds and compositions that can act as unique inhibitors of TLRs 9, 7, and/or 8 that can be tailored to the specific needs of the patient. Such new custom compounds and compositions will find use in many clinically relevant applications, including treating and preventing diseases and disorders with an immune stimulatory component.

BRIEF SUMMARY OF THE INVENTION

The invention provides antagonists of TLR7 and/or TLR9 that distinctly antagonize the in vitro and in vivo cytokine and chemokine profiles normally generated through TLR9, TLR7, and/or TLR8 stimulation. The ability to uniquely antagonize the cytokine and chemokine response to a TLR9, TLR7, and/or TLR8 agonist provides the ability to prevent and/or treat various disease conditions in a disease-specific and even a patient-specific manner.

Thus, the invention provides an immune regulatory oligonucleotide (IRO) compound selected from compound number 1 through compound number 15, as described below. The IRO compounds and compositions according to the invention preferentially inhibit TLR9-, TLR7-, and/or TLR8-mediated immune responses in various cell types and in various in vitro and in vivo experimental models, with each compound or composition providing a distinct immune inhibition profile.

The invention further provides for a pharmaceutical composition comprising an IRO compound according to the invention and a pharmaceutically acceptable carrier.

The invention further provides a method for inhibiting a TLR9, TLR7, and/or TLR8-mediated immune response in a vertebrate, or mammal, the method comprising administering to the mammal an IRO compound or composition according to the invention.

The invention further provides a method for inhibiting the activity of a TLR9, TLR7 and/or TLR8 agonist comprising administering an IRO compound according to the invention, wherein the IRO compound is administered at the same time, prior to or after the TLR agonist.

The invention further provides a method for therapeutically treating a vertebrate, or mammal, having a disease or disorder wherein inhibition of TLR9, TLR7, and/or TLR8 would be beneficial, such method comprising administering to the mammal an IRO compound according to the invention.

The invention further provides a method for preventing a disease or disorder in a vertebrate, or mammal, wherein inhibition of TLR9, TLR7, and/or TLR8 would be beneficial, such method comprising administering to the vertebrate or mammal an IRO compound according to the invention.

BRIEF DESCRIPTION OF THE DRAWINGS

FIG. 3 depicts the 50% inhibitory concentration ($IC_{50}$) values of TLR9, TLR7, TLR8 antagonist according to the invention in cell culture assays described in Example 4.

DETAILED DESCRIPTION OF THE PREFERRED EMBODIMENTS

Figure 1:
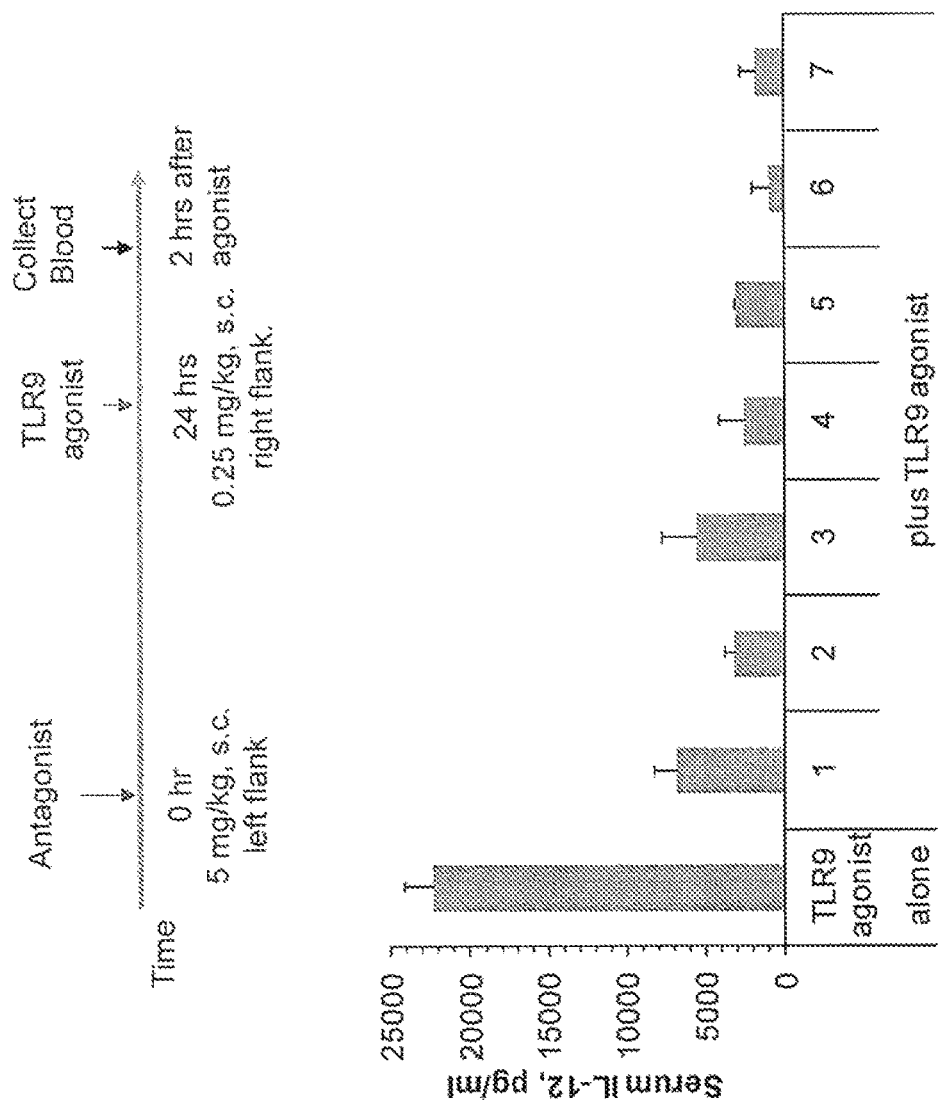
FIG. 1 depicts the ability of TLR7/9 antagonists according to the invention to inhibit TLR9-induced cytokines in vivo in mice treated according to Example 3. The data more generally demonstrate the ability of TLR antagonists according to the invention to inhibit TLR9-induced cytokines in vivo.

The present invention relates to the therapeutic use of oligonucleotide-based compounds as immune modulatory agents for immunotherapy applications. The invention provides oligonucleotide-based compounds that provide distinct immune inhibition profiles through their interaction with TLR9, TLR7, and/or TLR8. Specifically, the invention provides Immune Regulatory Oligonucleotide (IRO) compounds as antagonists of toll-like receptors 9, 7, and/or 8 (TLR9, TLR7, and/or TLR8) to inhibit and/or suppress a TLR9-, TLR7-, and/or TLR8-mediated immune response. These IROs have chemical modifications, and/or internucleotide linkages that provide their inhibition or suppression of TLR9-, TLR7-, and/or TLR8-mediated signaling in response to endogenous and/or exogenous TLR ligands or agonists. The references cited herein reflect the level of knowledge in the field and are hereby incorporated by reference in their entirety. Any conflicts between the teachings of the cited references and this specification shall be resolved in favor of the latter.

The invention further provides methods for inhibiting an immune response caused by TLR9, TLR7, and/or TLR8, which and can be used for immunotherapy applications such as, but not limited to, treatment of cancer, autoimmune disorders, asthma, respiratory allergies, food allergies, skin allergies, systemic lupus erythematosus (SLE), arthritis, pleurisy, chronic infections, inflammatory diseases, inflammatory bowel syndrome, sepsis, and bacteria, parasitic, and viral infections in adult and pediatric human and veterinary applications. Thus, the invention provides IRO compounds having optimal levels of immune modulatory effect for immunotherapy and methods for making and using such compounds. In addition, IRO compounds of the invention are useful in combination with, for example, vaccines, antigens, antibodies, allergens, chemotherapeutic agents (both chemotherapy and targeted therapies), and/or antisense oligonucleotides for prevention and treatment of diseases.

Definitions

The term "oligonucleotide" generally refers to a polynucleoside comprising a plurality of linked nucleoside units. Such oligonucleotides can be obtained from existing nucleic acid sources, including genomic or cDNA, but are preferably produced by synthetic methods. In preferred embodiments each nucleoside unit can encompass various chemical modifications and substitutions as compared to wild-type oligonucleotides, including but not limited to modified nucleoside base and/or modified sugar unit. Examples of chemical modifications are known to the person skilled in the art and are described, for example, in Uhlmann, E. et al. (1990) Chem. Rev. 90:543; "Protocols for Oligonucleotides and Analogs" Synthesis and Properties & Synthesis and Analytical Techniques, S. Agrawal, Ed, Humana Press, Totowa, USA 1993; and Hunziker, J. et al. (1995) Mod. Syn. Methods 7:331-417; and Crooke, S. et al. (1996) Ann. Rev. Pharm. Tox. 36:107-129. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate or phosphorodithioate linkages or combinations thereof.

The term "2'-substituted ribonucleoside" or "2'-substituted arabinoside" generally includes ribonucleosides or arabinonucleosides in which the hydroxyl group at the 2' position of the pentose moiety is substituted to produce a 2'-substituted or 2'-O-substituted ribonucleoside. In certain embodiments, such substitution is with a lower hydrocarbyl group containing 1-6 saturated or unsaturated carbon atoms, with a halogen atom, or with an aryl group having 6-10 carbon atoms, wherein such hydrocarbyl, or aryl group may be unsubstituted or may be substituted, for example, with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation 2'-amino, 2'-fluoro, 2'-allyl, 2'-O-alkyl and 2'-propargyl ribonucleosides or arabinosides, 2'-O-methylribonucleosides or 2'-O-methylarabinosides and 2'-O-methoxyethoxyribonucleosides or 2'-O-methoxyethoxyarabinosides.

The term "3'", when used directionally, generally refers to a region or position in a polynucleotide or oligonucleotide 3' (downstream) from another region or position in the same polynucleotide or oligonucleotide.

The term "5'", when used directionally, generally refers to a region or position in a polynucleotide or oligonucleotide 5'

(upstream) from another region or position in the same polynucleotide or oligonucleotide.

The term "about" generally means that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above.

The term "agonist" generally refers to a substance that binds to a receptor of a cell and induces a response. An agonist often mimics the action of a naturally occurring substance such as a ligand.

The term "antagonist" generally refers to a substance that attenuates or inhibits the effects of an agonist or ligand.

The term "adjuvant" generally refers to a substance which, when added to an immunogenic agent such as vaccine or antigen, enhances or potentiates an immune response to the agent in the recipient host upon exposure to the mixture.

The term "airway inflammation" generally includes, without limitation, asthma.

The term "allergen" generally refers to an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic immune response upon exposure to the molecule.

The term "allergy" generally refers to an inappropriate immune response characterized by inflammation and includes, without limitation, food allergies and respiratory allergies.

The term "antigen" generally refers to a substance that is recognized and selectively bound by an antibody or by a T cell antigen receptor, resulting in induction of an immune response. Antigens may include but are not limited to peptides, proteins, nucleosides, nucleotides, and combinations thereof. Antigens may be natural or synthetic and generally induce an immune response that is specific for that antigen.

The terms "autoimmune disease" and autoimmune disorder" generally refer to diseases or disorders in which "self" components undergo attack by the immune system.

The term "TLR-mediated disease" or TLR-mediated disorder" generally means any pathological condition for which activation of one or more TLRs is a contributing factor. Such conditions include but are not limited, cancer, autoimmune diseases or disorders, airway inflammation, inflammatory diseases or disorders, infectious diseases, skin disorders, allergy, asthma or diseases caused by a pathogen.

The term "physiologically acceptable" generally refers to a material that does not interfere with the effectiveness of an IRO compound or composition according to the invention and that is compatible with a biological system such as a cell, cell culture, tissue or organism. Preferably, the biological system is a living organism, such as a vertebrate, or mammal.

The term "carrier" generally encompasses any excipient, diluent, filler, salt, buffer, stabilizer, solubilizer, oil, lipid, lipid containing vesicle, microspheres, liposomal encapsulation or other material well known in the art for use in pharmaceutical formulations. It will be understood that the characteristics of the carrier, excipient or diluent will depend on the route of administration for a particular application. The preparation of pharmaceutically acceptable formulations containing these materials is described in, for example, *Remington's Pharmaceutical Sciences,* 18th Edition, ed. A. Gennaro, Mack Publishing Co., Easton, Pa., 1990.

The term "co-administration" generally refers to the administration of at least two different substances sufficiently close in time to modulate, suppress or inhibit an immune response. Co-administration refers to simultaneous administration, as well as temporally spaced order of up to several days apart, of at least two different substances in any order, either in a single dose or separate doses.

The term "complementary" generally means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

The term an "effective amount" or a "sufficient amount" generally refers to an amount sufficient to affect a desired biological effect, such as beneficial results. Thus, an "effective amount" or "sufficient amount" will depend upon the context in which it is being administered. In the context of administering a compound or composition that modulates an immune response to a co-administered antigen, an effective amount of an IRO compound or composition according to the invention and antigen is an amount sufficient to achieve the desired modulation, inhibition or suppression as compared to the immune response obtained when the antigen is administered alone. An effective amount may be administered in one or more administrations.

The term "in combination with" generally means in the course of treating a disease or disorder in a patient, administering an IRO compound or composition according to the invention and an agent useful for treating the disease or disorder that does not diminish the immune inhibitory effect of the IRO compound or composition according to the invention. Such combination treatment may also include more than a single administration of an IRO compound or composition according to the invention and/or independently an agent. The administration of the IRO compound or composition according to the invention and/or the agent may be by the same or different routes.

The term "individual" or "subject" or "vertebrate" generally refers to a mammal. Mammals generally include, but are not limited to, humans, non-human primates, rats, mice, cats, dogs, horses, cattle, cows, pigs, sheep, and rabbits.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. Examples of kinase inhibitors include sorafenib (Nexavar®), Sutent®, dasatinib, Dasatinib™, Zactima™, Tykerb™ and ST1571.

The term "nucleoside" generally refers to compounds consisting of a sugar, usually ribose or deoxyribose, and a purine or pyrimidine base.

The term "nucleotide" generally refers to a nucleoside comprising a phosphate group attached to the sugar.

As used herein, the term "pyrimidine nucleoside" refers to a nucleoside wherein the base component of the nucleoside is a pyrimidine base (e.g., cytosine (C) or thymine (T) or Uracil (U)). Similarly, the term "purine nucleoside" refers to a nucleoside wherein the base component of the nucleoside is a purine base (e.g., adenine (A) or guanine (G)).

The terms "analog" or "derivative" can be used interchangeable to generally refer to any purine and/or pyrimidine nucleotide or nucleoside that has a modified base and/or sugar. A modified base is a base that is not guanine, cytosine, adenine, thymine or uracil. A modified sugar is any sugar that is not ribose or 2'deoxyribose and can be used in the backbone for an oligonucleotide.

The term "inhibiting" generally refers to a decrease in or a prevention of a response or qualitative difference in a response, which could otherwise arise from eliciting and/or stimulation of a response.

The term "non-nucleotide linker" generally refers to any linkage or moiety that can link or be linked to the oligonucleotides other than through a phosphorous-containing linkage. Preferably such linker is from about 2 angstroms to about 200 angstroms in length.

The term "nucleotide linkage" generally refers to a direct 3'-5' linkage that directly connects the 3' and 5' hydroxyl groups of two nucleosides through a phosphorous-containing linkage.

The term "treatment" generally refers to an approach intended to obtain a beneficial or desired results, which may include alleviation of symptoms and/or delaying and/or ameliorating the progression of a disease or disorder.

In a first aspect, the invention provides immune regulatory oligonucleotide (IRO) compounds as shown in Table 2. The term "IRO" refers to an immune regulatory oligonucleotide-based compound that is an antagonist for TLR9, TLR7, and/or TLR8. In Table 2, the IRO compounds have all phosphorothioate (PS) linkages and all nucleotides are deoxynucleotides, unless otherwise indicated.

TABLE 2

| IRO compound # | Sequence/Structure/SEQ ID NO |
|---|---|
| 1 | 5'-CTATCT<u>GUC</u>*G1TTCACT<u>GU</u>-3'<br>(SEQ ID NO 1) |
| 2 | 5'-CCATCT<u>GUC</u>*G1TTCACT<u>GU</u>-3'<br>(SEQ ID NO 2) |
| 3 | 5'-CAATCT<u>GUC</u>*G1TTCACT<u>GU</u>-3'<br>(SEQ ID NO 3) |
| 4 | 5'-CTATCT<u>GUC</u>*G1TTCTC<u>UGU</u>-3'<br>(SEQ ID NO 4) |
| 5 | 5'-CTATC<u>UGUC</u>*G1TTCTCT<u>GU</u>-3'<br>(SEQ ID NO 5) |
| 6 | 5'-C*TATC*T<u>GUC</u>*G1TTC*TC*T<u>GU</u>-3'<br>(SEQ ID NO 6) |
| 7 | 5'-CdUAdUCdU<u>GUC</u>*G1TTCdUCdU<u>GU</u>-3'<br>(SEQ ID NO 7) |
| 8 | 5'-CTATCT<u>GUC</u>G1TTCTCT<u>GU</u>-3'<br>(SEQ ID NO 8) |
| 9 | 5'-CTATCT<u>GUC</u>G1TTCTCT<u>GU</u>-3'<br>(SEQ ID NO 9) |
| 10 | 5'-CTATCT<u>GUC</u>*G1TTCTCT<u>GU</u>-3'<br>(SEQ ID NO 10) |
| 11 | 5'-CTATCT<u>GUC</u>*G1TTCTCT<u>GU</u>-3'<br>(SEQ ID NO 11) |

TABLE 2-continued

| IRO compound # | Sequence/Structure/SEQ ID NO |
|---|---|
| 12 | 5'-CTATCT<u>GUC</u>*G2TTCTCT<u>GU</u>-3'<br>(SEQ ID NO 12) |
| 13 | 5'-<u>C</u>TATCT<u>GUC</u>*G1TTCTCT<u>GU</u>-3'<br>(SEQ ID NO 13) |
| 14 | 5'-C6TATCT<u>GUC</u>*G1TTCTCT<u>GU</u>-3'<br>(SEQ ID NO 14) |
| 15 | 5'-C7TATCT<u>GUC</u>*G1TTCTCT<u>GU</u>-3'<br>(SEQ ID NO 15) |
| 16 | 5'-CTATCT<u>GUC</u>*G1TTCTCT<u>GU</u>-3'<br>(SEQ ID NO 16) |

G1 = 7-deaza-dG;
C* = 5-Me-dC;
<u>G</u> = 2'-O-Me-G;
<u>U</u> = 2'-O-Me-U;
dU = deoxy-U;
G2 = AraG;
<u>C</u> = 2'-O-Me-C;
<u>C</u>* = 2'-OMe-5-Me-C;
C6 = 2'-MOE-C;
C7 = 2'-O-Propargyl-C.

In preferred embodiments the IRO compound is not an antisense oligonucleotide.

In some embodiments, the oligonucleotides of the IRO compound can have from about 6 to about 35 nucleoside residues, preferably from about 9 to about 30 nucleoside residues, more preferably from about 11 to about 23 nucleoside residues. In some embodiments, the oligonucleotides have from about 6 to about 18 nucleotide residues. In some embodiments, the IRO compound is 18 nucleotide residues in length.

In some embodiments, the IRO compounds can be combined with one or more vaccines, antigens, antibodies, cytotoxic agents, allergens, antibiotics, antisense oligonucleotides, TLR antagonist, peptides, proteins, gene therapy vectors, DNA vaccines, adjuvants or kinase inhibitors.

In a second aspect, the invention provides a pharmaceutical composition comprising an IRO compound according to the invention and a physiologically acceptable carrier.

In embodiments of this aspect of the invention, the composition can further comprise one or more vaccines, antigens, antibodies, cytotoxic agents, allergens, antibiotics, antisense oligonucleotides, TLR antagonist, peptides, proteins, gene therapy vectors, DNA vaccines, adjuvants or kinase inhibitors.

In a third aspect, the invention provides methods for inhibiting or suppressing TLR9, TLR7-, and/or TLR8-mediated induction of an immune response in a mammal, such methods comprising administering to the mammal an IRO compound according to the invention. In some embodiments, the mammal is a human. In preferred embodiments, the IRO compound is administered to a mammal in need of immune suppression.

According to this aspect of the invention, an IRO compound is capable of suppressing a TLR9, TLR7-, and/or TLR8-based immune response to a further TLR ligand or TLR agonist. As discussed further in the Examples below, the activation of a TLR9, TLR7-, and/or TLR8-based immune response by a TLR agonist or TLR ligand (for example, an immune stimulatory oligonucleotide) can be antagonized, inhibited, suppressed or prevented by the simultaneous, pre- or post-administration of an IRO compound, and such antagonism, inhibition, suppression or prevention may be maintained for an extended period of time (for example, days) after administration. This beneficial property of the current invention has a unique advantage for the prevention and/or treatment of a disease or disorder. For example, application of certain TLR-agonists in the course of treating the disease may cause unwanted immune stimulation that an IRO compound could antagonize, suppress, inhibit or prevent. Administration of the IRO simultaneously, pre and/or post administration of the TLR-agonist may allow therapeutic benefits from the TLR-agonist while antagonizing, suppressing, inhibiting or preventing the unwanted side effect(s). Additionally, pre-administration of an IRO compound according to the invention could antagonize, suppress, inhibit or prevent an immune response (for example, an allergic reaction) to a subsequent or later challenge by a TLR-agonist. Preferably a TLR9, TLR7, and/or TLR8 agonist.

In the methods according to this aspect of the invention, administration of IRO compound according to the invention can be by any suitable route, including, without limitation, parenteral, mucosal delivery, oral, sublingual, transdermal, topical, inhalation, intragastric, intranasal, aerosol, intraocular, intratracheal, intrarectal, vaginal, by gene gun, dermal patch or in eye drop or mouthwash form. Administration of the therapeutic compositions of IRO compound can be carried out using known procedures at dosages and for periods of time effective to reduce symptoms or surrogate markers of the disease. When administered systemically, the therapeutic composition is preferably administered at a sufficient dosage to attain a blood concentration of IRO compound from about 0.0001 micromolar to about 100 micromolar. More preferably, systemic administration would be at a sufficient dosage to attain a blood concentration of the IRO compound from about 0.001 micromolar to about 10 micromolar. For localized administration, much lower concentrations than this may be effective, and much higher concentrations may be tolerated. Preferably, a total dosage of IRO compound ranges from about 0.001 mg per patient per day to about 200 mg per kg body weight per day. It may be desirable to administer the IRO compound according to the invention daily, every second day, every third day, every fourth day, every fifth day, every sixth day or weekly. It may be desirable to administer simultaneously, or sequentially, a therapeutically effective amount of one or more of the IRO containing therapeutic compositions of the invention to an individual as a single treatment episode.

The IRO compound may optionally be linked to and/or combined with one or more allergens and/or antigens (self or foreign), an immunogenic protein, such as keyhole limpet hemocyanin (KLH), cholera toxin B subunit, or any other immunogenic carrier protein. IRO can also be used in combination with other compounds (for example, adjuvants) including, without limitation, TLR agonists (e.g. TLR2 agonists, TLR4 agonists, and TLR9 agonists), Freund's incomplete adjuvant, KLH, monophosphoryl lipid A (MPL), alum, Merck alum adjuvant (MAA), and saponins, including QS-21 and imiquimod, or combinations thereof.

The methods according to this aspect of the invention are useful for model studies of the immune system. The methods are also useful for the prophylactic or therapeutic treatment of human or animal disease. For example, the methods are useful for pediatric, adult, and veterinary vaccine applications.

In a fourth aspect, the invention provides methods for therapeutically treating a patient having a disease or disorder wherein inhibition of TLR9, TLR7, and/or TLR8 would be beneficial, such methods comprising administering to the patient a IRO compound according to the invention. In various embodiments, the disease or disorder to be treated is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barre syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjogren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behcet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. Administration is carried out as described for the third aspect of the invention.

In a fifth aspect, the invention provides methods for preventing a disease or disorder wherein inhibition of TLR9, TLR7, and/or TLR8 would be beneficial, such methods comprising administering to the patient a IRO compound according to the invention. In various embodiments, the disease or disorder to be prevented is cancer, an autoimmune disorder, airway inflammation, inflammatory disorders, infectious disease, malaria, Lyme disease, ocular infections, conjunctivitis, skin disorders, psoriasis, scleroderma, cardiovascular disease, atherosclerosis, chronic fatigue syndrome, sarcoidosis, transplant rejection, allergy, asthma or a disease caused by a pathogen. Preferred autoimmune disorders include without limitation lupus erythematosus, multiple sclerosis, type I diabetes mellitus, irritable bowel syndrome, Crohn's disease, rheumatoid arthritis, septic shock, alopecia universalis, acute disseminated encephalomyelitis, Addison's disease, ankylosing spondylitis, antiphospholipid antibody syndrome, autoimmune hemolytic anemia, autoimmune hepatitis, Bullous pemphigoid, chagas disease, chronic obstructive pulmonary disease, coeliac disease, dermatomyositis, endometriosis, Goodpasture's syndrome, Graves' disease, Guillain-Barre syndrome, Hashimoto's disease, hidradenitis suppurativa, idiopathic thrombocytopenic purpura, interstitial cystitis, morphea, myasthenia gravis, narcolepsy, neuromyotonia, pemphigus, pernicious anaemia, polymyositis, primary biliary cirrhosis, schizophrenia, Sjogren's syndrome, temporal arteritis ("giant cell arteritis"), vasculitis, vitiligo, vulvodynia and Wegener's granulomatosis. Preferred inflammatory disorders include without limitation airway inflammation, asthma, autoimmune diseases, chronic inflammation, chronic prostatitis, glomerulonephritis, Behcet's disease, hypersensitivities, inflammatory bowel disease, reperfusion injury, rheumatoid arthritis, transplant rejection, ulcerative colitis, uveitis, conjunctivitis and vasculitis. Pathogens include bacteria, parasites, fungi, viruses, viroids, and prions. Administration is carried out as described for the third aspect of the invention.

In any of the methods according to the third, fourth or fifth aspect of the invention, the IRO compound can be administered in combination with any other agent useful for treating or preventing the disease or condition that does not abolish the immune antagonist, inhibitory, suppression or prevention effect or activity of the IRO compound. In any of the methods according to the invention, the agent useful for treating or preventing the disease or condition includes, but is not limited to, one or more vaccines, antigens, antibodies, cytotoxic agents, allergens, antibiotics, antisense oligonucleotides, TLR antagonist, peptides, proteins, gene therapy vectors, DNA vaccines, adjuvants or kinase inhibitors. For example, in the treatment of cancer, it is contemplated that the IRO compound may be administered in combination with one or more chemotherapeutic compound, targeted therapeutic agent and/or monoclonal antibody; and in preventing a disease, it is contemplated that the IRO compound may be administered in combination with one or more vaccine. Alternatively, the agent can include DNA vectors encoding for antigen or allergen. In these embodiments, the IRO compounds of the invention can variously act as adjuvants and/or produce direct immune modulatory effects.

The following examples are intended to further illustrate certain exemplary embodiments of the invention and are not intended to limit the scope of the invention. For example, representative TLR-ligands are shown in the following examples, but do not limit the scope of ligands to which the IROs of the invention act as antagonists.

Example 1

Synthesis of Oligonucleotides Containing Immune Regulatory Moieties

All IRO compounds of the invention were synthesized according to standard procedures (see e.g. U.S. Patent Publication No. 20040097719).

Oligonucleotides were synthesized on a 1 μM scale using an automated DNA synthesizer (Expedite 8909; PerSeptive Biosystems, Framingham, Mass.), following standard linear synthesis or parallel synthesis procedures (see e.g. FIGS. 5 and 6 of U.S. Patent Publication No. 20040097719).

Deoxyribonucleoside phosphoramidites were obtained from (Aldrich-Sigma, St Louis, Mo.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). .beta.-L-2'-deoxyribonucleoside phosphoramidite, .alpha.-2'-deoxyribonucleoside phosphoramidite, mono-DMT-glycerol phosphoramidite and di-DMT-glycerol phosphoramidite were obtained from ChemGenes (Willmington, Mass.). (4-Aminobutyl)-1,3-propanediol phosphoramidite was obtained from Clontech (Palo Alto, Calif.). Arabinoguanosine, was obtained from Reliable Pharmaceutical (St. Louis, Mo.). Arabinoguanosine phosphoramidite was synthesized at Idera Pharmaceuticals, Inc. (Cambridge, Mass.) (Noronha et al. (2000) Biochem., 39:7050-7062).

All nucleoside phosphoramidites were characterized by $^{31}$P and $^1$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

In Vivo Inhibition of TLR7 and TLR9 Stimulation

C57BL/6 mice were injected s.c. at left underarm with 5 mg/kg of an IRO compound at 0 hours and 0.25 mg/kg TLR9 agonist or 10 mg/kg TLR7 agonist at 24 hours. Serum samples were taken at 2 hours after injection of the TLR9 or TLR7 agonist and IL-12 concentration was determined by ELISA. The results are shown in Table 3. These results demonstrate that an IRO compounds according to the invention can inhibit TLR7 and/or TLR9 activity in vivo, and more generally that IRO compounds according to the invention can inhibit TLR activation.

TABLE 3

| Antagonist Activity in vivo in mice | | |
|---|---|---|
| Oligo No. Sequences and Modification | % Inhibition of TLR9 agonist induced IL-12 | % Inhibition of TLR7 agonist induced IL-12 |
| 1  5'-CTATCT<u>GU</u>C*G1TTCACT<u>GU</u>-3' (SEQ ID NO: 1) | 69.3 | 80.4 |
| 2  5'-CCATCT<u>GU</u>C*G1TTCACT<u>GU</u>-3' (SEQ ID NO: 2) | 85.4 | 80.9 |
| 3  5'-CAATCT<u>GU</u>C*G1TTCACT<u>GU</u>-3' (SEQ ID NO: 3) | 75.2 | 91.1 |
| 4  5'-CTATCT<u>GU</u>C*G1TTCTC<u>UGU</u>-3' (SEQ ID NO: 4) | 88.7 | 86.9 |
| 5  5'-CTATC<u>UGU</u>C*G1TTCTCT<u>GU</u>-3' (SEQ ID NO: 5) | 86.3 | 76.8 |
| 6  5'-C*TATC*T<u>GU</u>C*G1TTC*TC*T<u>GU</u>-3' (SEQ ID NO: 6) | 95.5 | 94.1 |
| 7  5'-CdUAdUCd<u>UGU</u>C*G1TTCdUCd<u>UGU</u>-3' (SEQ ID NO: 7) | 91.9 | 79.1 |
| 9  5'-CTATCT<u>GU</u>CG1TTCTCT<u>GU</u>-3' (SEQ ID NO: 9) | 70.5 | 84.4 |
| 10 5'-CTATCT<u>GU</u>C*G1TTCTCT<u>GU</u>-3' (SEQ ID NO: 10) | 79.4 | 84.3 |
| 12 5'-CTATCT<u>GU</u>C*G2TTCTCT<u>GU</u>-3' (SEQ ID NO: 12) | 69.3 | 78.0 |
| 13 5'-<u>C</u>TATCT<u>GU</u>C*G1TTCTCT<u>GU</u>-3' (SEQ ID NO: 13) | 69.8 | 29.9 |
| 14 5'-C6TATCT<u>GU</u>C*G1TTCTCT<u>GU</u>-3' (SEQ ID NO: 14) | 66.1 | 33.7 |
| 15 5'-C7TATCT<u>GU</u>C*G1TTCTCT<u>GU</u>-3' (SEQ ID NO: 15) | 67.8 | 42.6 |

Example 3

TLR7/TLR9 In Vivo Antagonist Study

Figure 2:
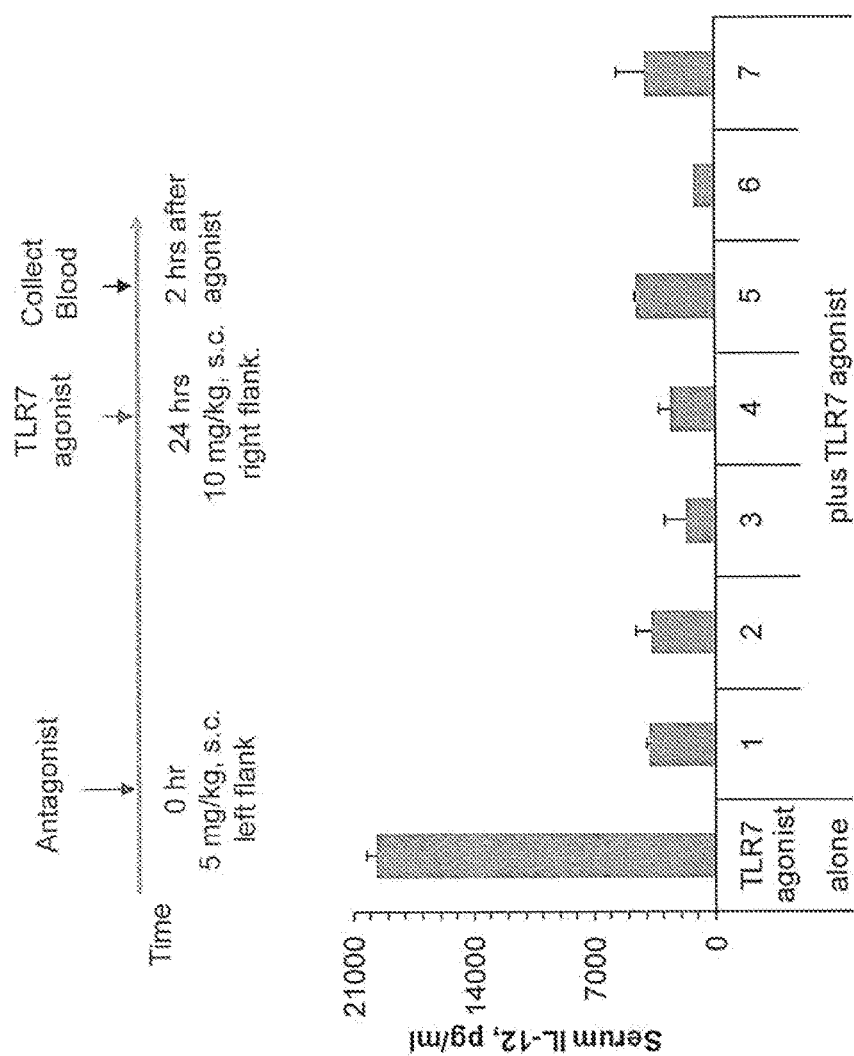
FIG. 2 depicts the ability of TLR7/9 antagonists according to the invention to inhibit TLR7-induced cytokines in vivo in mice treated according to Example 3. The data more generally demonstrate the ability of TLR antagonists according to the invention to inhibit TLR7-induced cytokines in vivo.

Female C57BL/6 mice (2/group) were s.c injected with 5 mg/kg antagonist compound at 0 hr in the right flank. The mice were then injected with TLR9 (0.25 mg/kg) or TLR7 (10 mg/kg) agonists at 24 hrs in the left flank. Blood was collected by orbital bleeding 2 hrs post the agonist administration. Cytokine/chemokine responses were then evaluated in serum samples by multiplex assays using the Luminex xMAP system. Results are shown in FIGS. 1 and 2.

Example 4

Cell Culture Assays of HEK293 Cells Expressing TLR4, 7, 8 and 9

Human embryonic kidney (HEK) 293 cells stably expressing human TLR4/CD14/MD-2 or mTLR9 and HEK293XL cells stably expressing human TLR7 or TLR8 were obtained from Invivogen (San Diego, Calif.). HEK cells were transiently transfected with reporter gene (SEAP, Invivogen) for 6 h. Appropriate TLR agonists were added to the cultures in the presence or absence of various concentrations of antagonists, and the cultures were continued for 18 hours. At the end of the treatment, 20 ml of culture supernatant was taken from each treatment and tested for SEAP activity using 150 ml of Quanti-Blue substrate following manufacturer's protocol (Invivogen). The results are calculated as fold change in NF-κB activation over PBS-treated cells and 50% inhibitory concentration ($IC_{50}$) values were determined. Results are shown in FIG. 3.

What is claimed:

1. A method for therapeutically treating a mammal having an inflammatory disorder, comprising administering to the mammal an immune regulatory oligonucleotide (IRO), wherein the IRO is 5'-C*TATC*TGUC*G1TTC*TC*TGU-3' (SEQ ID NO: 6), and wherein G1=7-deaza-dG; C*=5-Me-dC; G=2'-O-Me-G; and U=2'-O-Me-U.

2. The method according to claim 1, wherein the inflammatory disorder is selected from the group consisting of airway inflammation, asthma, chronic inflammation, chronic prostatitis, glomerulonephritis, Behcet's disease, hypersensitivity, inflammatory bowel disease, reperfusion injury, rheumatoid arthritis, transplant rejection, ulcerative colitis, conjunctivitis, and vasculitis.

3. A method for therapeutically treating a mammal having inflammatory bowel disease, comprising administering to the mammal an immune regulatory oligonucleotide (IRO), wherein the IRO is 5'-C*TATC*TGUC*G1TTC*TC*TGU-3' (SEQ ID NO: 6), and wherein G1=7-deaza-dG; C*=5-Me-dC; G=2'-O-Me-G; and U=2'-O-Me-U.

4. A method for therapeutically treating a mammal having ulcerative colitis, comprising administering to the mammal an immune regulatory oligonucleotide (IRO), wherein the IRO is 5'-C*TATC*TGUC*G1TTC*TC*TGU-3' (SEQ ID NO: 6), and wherein G1=7-deaza-dG; C*=5-Me-dC; G=2'-O-Me-G; and U=2'-O-Me-U.

5. The method according to claim 1, wherein the mammal is a human.

6. The method according to claim 2, wherein the mammal is a human.

7. The method according to claim 3, wherein the mammal is a human.

8. The method according to claim 4, wherein the mammal is a human.

9. The method according to claim 5, wherein the IRO is administered in combination with one or more vaccines, antigens, antibodies, cytotoxic agents, allergens, antibiotics, antisense oligonucleotides, Toll-like receptor antagonists, peptides, proteins, gene therapy vectors, DNA vaccines, adjuvants, or kinase inhibitors.

10. The method according to claim 5, wherein the administering of the IRO is daily.

11. The method according to claim 5 or 10, wherein the administering of the IRO is orally.

12. The method according to claim 6, wherein the IRO is administered in combination with one or more vaccines, antigens, antibodies, cytotoxic agents, allergens, antibiotics, antisense oligonucleotides, Toll-like receptor antagonists, peptides, proteins, gene therapy vectors, DNA vaccines, adjuvants, or kinase inhibitors.

13. The method according to claim 6, wherein the administering of the IRO is daily.

14. The method according to claim 6 or 13, wherein the administering of the IRO is orally.

15. The method according to claim 7, wherein the IRO is administered in combination with one or more vaccines, antigens, antibodies, cytotoxic agents, allergens, antibiotics, antisense oligonucleotides, Toll-like receptor antagonists, peptides, proteins, gene therapy vectors, DNA vaccines, adjuvants, or kinase inhibitors.

16. The method according to claim 7, wherein the administering of the IRO is daily.

17. The method according to claim 7 or 16, wherein the administering of the IRO is orally.

18. The method according to claim 8, wherein the IRO is administered in combination with one or more vaccines, antigens, antibodies, cytotoxic agents, allergens, antibiotics, antisense oligonucleotides, Toll-like receptor antagonists, peptides, proteins, gene therapy vectors, DNA vaccines, adjuvants, or kinase inhibitors.

19. The method according to claim 8, wherein the administering of the IRO is daily.

20. The method according to claim 8 or 19, wherein the administering of the IRO is orally.

* * * * *

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 1
ctatctgucg ttcactgu                                                 18

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 2
ccatctgucg ttcactgu                                                 18

<210> SEQ ID NO 3
```

```
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 3
caatctgucg ttcactgu                                                 18

<210> SEQ ID NO 4
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (16)..(18)
<223> OTHER INFORMATION: 2'-O-Me

<400> SEQUENCE: 4
ctatctgucg ttctcugu                                                 18

<210> SEQ ID NO 5
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (6)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 5
```
ctatcugucg ttctctgu                                                       18

<210> SEQ ID NO 6
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: 5-methyl-dC
<220> FEATURE:
<221> NAME/KEY: modified_base
<222> LOCATION: (5)..(5)
<223> OTHER INFORMATION: 5-methyl-dC
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (13)..(13)
<223> OTHER INFORMATION: 5-methyl-dC
<220> FEATURE:
<221> NAME/KEY: modified_base
<222> LOCATION: (15)..(15)
<223> OTHER INFORMATION: 5-methyl-dC
<220> FEATURE:
<221> NAME/KEY: modified_base
<222> LOCATION: (17)..(18)
<223> OTHER INFORMATION: 2'-O-Me

<400> SEQUENCE: 6
ctatctgucg ttctctgu                                                       18

<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: deoxy-U
<220> FEATURE:
<221> NAME/KEY: modified_base
<222> LOCATION: (4)..(4)
<223> OTHER INFORMATION: deoxy-U
<220> FEATURE:
<221> NAME/KEY: modified_base
<222> LOCATION: (6)..(6)
<223> OTHER INFORMATION: deoxy-U
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:

```
<221> NAME/KEY: modified_base
<222> LOCATION: (14)..(14)
<223> OTHER INFORMATION: deoxy-U
<220> FEATURE:
<221> NAME/KEY: modified_base
<222> LOCATION: (16)..(16)
<223> OTHER INFORMATION: deoxy-U
<220> FEATURE:
<221> NAME/KEY: modified_base
<222> LOCATION: (17)..(18)
<223> OTHER INFORMATION: 2'-O-Me

<400> SEQUENCE: 7
cuaucugucg ttcucugu                                                         18

<210> SEQ ID NO 8
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(9)
<223> OTHER INFORMATION: 2'-O-Me
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 8
ctatctgucg ttctctgu                                                         18

<210> SEQ ID NO 9
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)..(9)
<223> OTHER INFORMATION: 2'-O-Me
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 9
ctatctgucg ttctctgu                                                         18

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 2'-O-Me-5-Me-C
```

```
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 10
ctatctgucg ttctctgu                                                 18

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (8)..(8)
<223> OTHER INFORMATION: 2'-O-Me
<220> FEATURE:
<221> NAME/KEY: modified_base
<222> LOCATION: (9)..(9)
<223> OTHER INFORMATION: 2'-O-Me-5-Me-C
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 11
ctatctgucg ttctctgu                                                 18

<210> SEQ ID NO 12
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: arabinoguanosine
<220> FEATURE:
<221> NAME/KEY: modified_base
<222> LOCATION: (17)..(18)
<223> OTHER INFORMATION: 2'-O-Me

<400> SEQUENCE: 12
ctatctgucg ttctctgu                                                 18

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
```

```
<223> OTHER INFORMATION: 2'-O-Me
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 13
ctatctgucg ttctctgu                                                      18

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: 2'-MOE
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 14
ctatctgucg ttctctgu                                                      18

<210> SEQ ID NO 15
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: 2'-O-propargyl
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl=dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
```

```
<222> LOCATION: (17)..(18)
<223> OTHER INFORMATION: 2'-O-Me

<400> SEQUENCE: 15
ctatctgucg ttctctgu                                                    18

<210> SEQ ID NO 16
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (7)..(8)
<223> OTHER INFORMATION: 2'-O-Me
<220> FEATURE:
<221> NAME/KEY: modified_base
<222> LOCATION: (9)..(9)
<223> OTHER INFORMATION: 5-methyl-dC
<220> FEATURE:
<221> NAME/KEY: modified_base
<222> LOCATION: (10)..(10)
<223> OTHER INFORMATION: 7-deaza-dG
<220> FEATURE:
<221> NAME/KEY: modified_base
<222> LOCATION: (17)..(18)
<223> OTHER INFORMATION: 2'-O-Me

<400> SEQUENCE: 16
ctatctgucg ttctctgu                                                    18
```